United States Patent [19]
Griebel

[11] Patent Number: 6,120,441
[45] Date of Patent: Sep. 19, 2000

[54] METHOD AND DEVICE FOR QUANTITATIVE ANALYSIS OF SLEEP DISTURBANCES

[75] Inventor: Peter Griebel, Pflaumdorf, Germany

[73] Assignee: MAP Medizintechnik fur Arzt und Patient GmbH, Martinsried, Germany

[21] Appl. No.: 09/051,545

[22] PCT Filed: Oct. 16, 1996

[86] PCT No.: PCT/EP96/04497

§ 371 Date: Jul. 2, 1998

§ 102(e) Date: Jul. 2, 1998

[87] PCT Pub. No.: WO97/14354

PCT Pub. Date: Apr. 24, 1997

[30] Foreign Application Priority Data

Oct. 16, 1995 [DE] Germany ............... 195 38 473

[51] Int. Cl.⁷ .................................................. A61B 5/00
[52] U.S. Cl. ............................... 600/300; 600/532
[58] Field of Search ..................... 128/204.21–204.23; 600/300, 301, 529–539, 481–500

[56] References Cited

U.S. PATENT DOCUMENTS

| | | | |
|---|---|---|---|
| 3,734,086 | 5/1973 | Phelps | 128/2.05 P |
| 4,802,485 | 2/1989 | Bowers et al. | 128/633 |
| 5,033,472 | 7/1991 | Sato et al. | 128/691 |
| 5,105,354 | 4/1992 | Nishimura | 364/413.03 |
| 5,245,995 | 9/1993 | Sullivan et al. | 128/204.23 |
| 5,385,144 | 1/1995 | Yamanishi et al. | 126/633 |
| 5,743,856 | 4/1998 | Oka et al. | 600/485 |
| 5,769,084 | 6/1998 | Katz et al. | 600/500 |

FOREIGN PATENT DOCUMENTS

| | | | |
|---|---|---|---|
| 356603 | 3/1990 | European Pat. Off. | A61B 5/04 |
| 450341A | 10/1991 | European Pat. Off. | A61B 5/0452 |
| 3248222A | 6/1984 | Germany | A61B 5/10 |
| 3921784A | 1/1991 | Germany | A61B 5/00 |
| 9200249.8 | 5/1992 | Germany | A61B 5/08 |
| 69204190.6 | 7/1992 | Germany | A61B 5/08 |
| 4138702A | 9/1992 | Germany | A61B 5/08 |
| WO8802237A | 4/1988 | WIPO | A61B 5/10 |
| WO9109372A | 6/1991 | WIPO | G06F 15/42 |

OTHER PUBLICATIONS

R. Kurz "Medizinische Messtechnik und Biosignalverarbeitung in der kardiologischen Diagnostik" pp 122–129 (1984).

*Primary Examiner*—Cary O'Connor
*Assistant Examiner*—Michael Astoriao
*Attorney, Agent, or Firm*—Ohlandt, Greeley, Ruggiero & Perle, LLP; George W. Rauchfuss

[57] ABSTRACT

The invention relates to an apparatus and a method for the stationary and ambulant detection, recording and quantitative analysis of sleep disorders, sleep-related respiratory disturbances, cardiac rhythm disturbances, myoclonia, variations in blood pressure, depth of sleep parameters, movement parameters and disorder parameters for the quality control of diagnoses. According to the invention, various sensors detect a patient's body functions which are stored in a recorder. The stored data are then transferred to a computer where they are analyzed and evaluated.

21 Claims, 11 Drawing Sheets

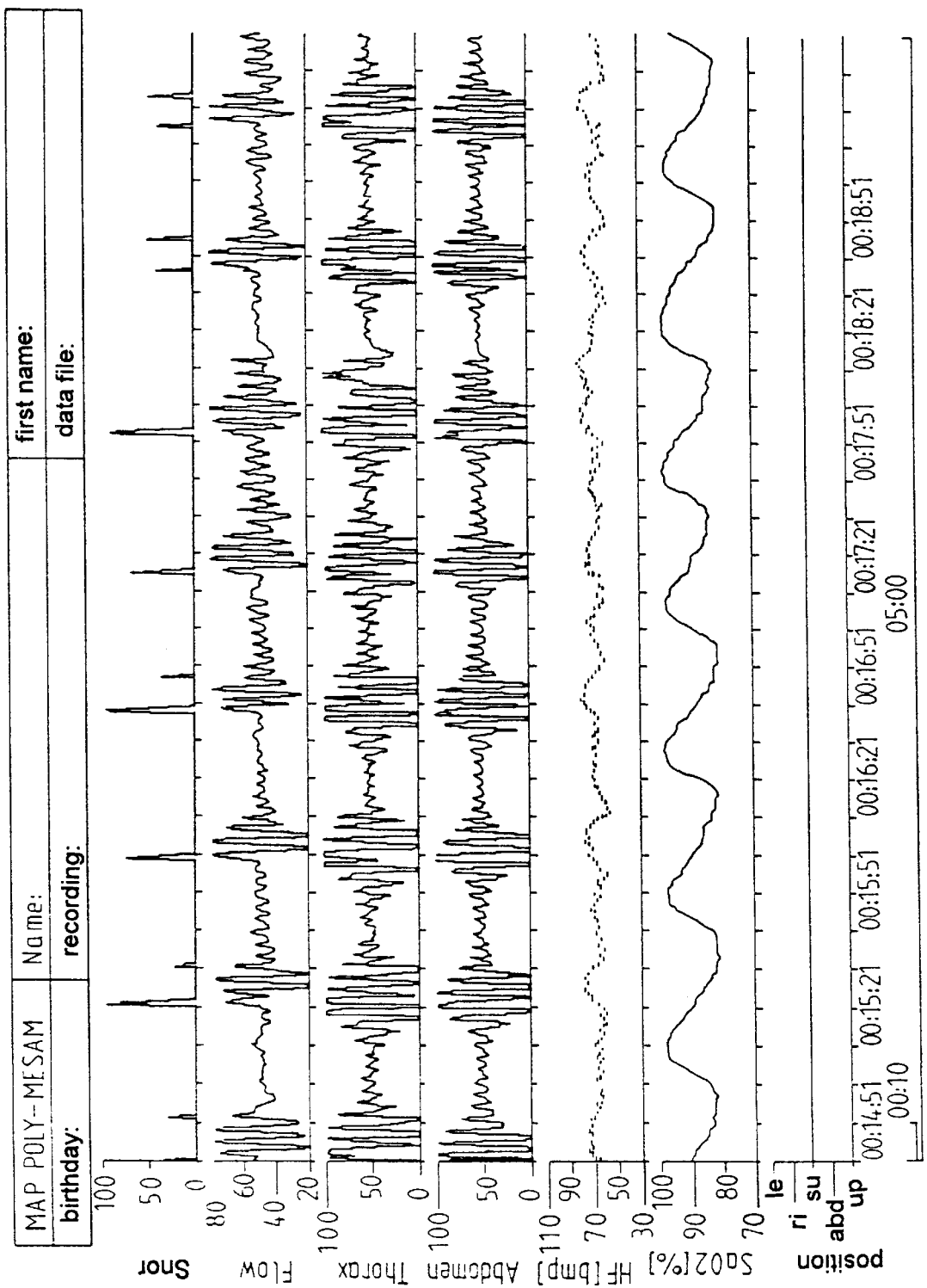

Fig. 2

| MAP Medizintechnik für Arzt u. Patient | POLY-MESAM S/W: V 1.1, H/W: PolyMesam |
|---|---|

| patient: | birthday: | PID: |
|---|---|---|
| recording: | data file: | doctor: | a)

1. patient data

| file name : | doctor : |
|---|---|
| name : | PID : |
| first name : | sex : |
| birthday : | height : |
| street : | weight : |
| city : | Broca index : |
| telephone : | diastol. pressure : |

2. recording

| recording period | : | 26.9.1995 : 20:00:02 - 07:01:02 duration: 11:01:00 |
|---|---|---|
| evaluation period | : | 21:59:52 - 06:00:02 duration: 8.00.10 |
| $SaO_2$ artifacts | : | 0:04:06 (0,85% of the evaluation period) | b)

A. indices

| parameter | phases/hour | correlation to the RDI |
|---|---|---|
| RDI | 60 | — |
| apnea index | 47 | 80 % |
| hypopnea index | 12 | 20 % |
| desaturation index | 58 | 66 % |
| heart rate variation index | 0 | 0 % |
| mobility index | 3 | 0 % |

Fig. 3

| MAP Medizintechnik für Arzt u. Patient | POLY-MESAM S/W: V 1.1, H/W: PolyMesam |
|---|---|

| patient: | birthday: | PID: |
|---|---|---|
| recording: | data file: | doctor: | a)

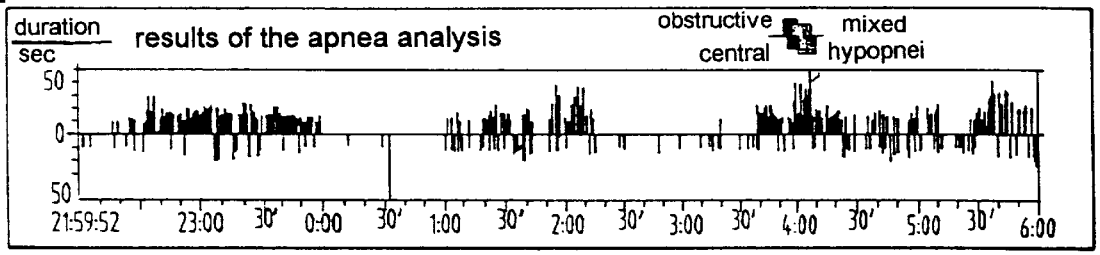

b)

| B. results of the apnea analysis | | | | | | | |
|---|---|---|---|---|---|---|---|
| class | all | 10...20s | > 20 s | > 40 s | av. duration | max dur. | Index |
| obstructive | 140 | 121 | 19 | 2 | 16 s ± 7 | 54 s | 17 |
| mixed | 196 | 145 | 51 | 1 | 19 s ± 6 | 46 s | 24 |
| central | 44 | 40 | 4 | 0 | 15 s ± 4 | 23 s | 5 |
| total | 380 | 306 | 74 | 3 | 17 s ± 6 | 54 s | 47 |
| hypopnea | 97 | 96 | 1 | 1 | 14 s ± 8 | 86 s | 12 | c)

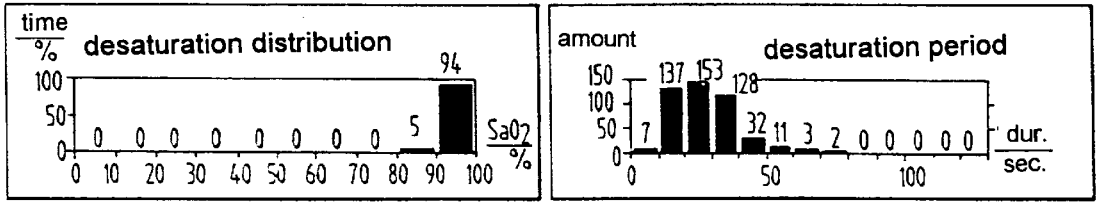

d)

| C. results of the desaturation analysis | | |
|---|---|---|
| oxygen saturation | SaO2 < = 100 % | SaO2 < = 90 % |
| lowest desaturation | 71 % | 71 % |
| average minimum | 90 % ± 3 | 87 % ± 0 |
| average saturation | 95 % ± 2 | 87 % ± 0 |
| average basal saturation | 96 % ± 3 | 87 % ± 0 |
| maximum duration | 76 s | 76 s |
| average duration | 26 s ± 2 | 31 s ± 0 |
| desaturation amount | 465 | 172 |
| desaturation index | 58 / h | 21 / h |

Fig. 4

| MAP Medizintechnik für Arzt u. Patient | POLY-MESAM S/W: V1.1, H/W: PolyMesam |

| Patient: | birthday: | PID: |
|---|---|---|
| recording: | data file: | doctor: | a)

| D. results of the body position sensor, absolute and apnea-related ||||||
|---|---|---|---|---|---|
| body position | time used | apnei amount | index | av. duration of apnei | apnei/ position |
| left | 1:10:25 | 72 | 9 | 20s ± 9 | 19% |
| right | 1:56:35 | 122 | 15 | 16s ± 5 | 32% |
| supine pos. | 2:20:40 | 173 | 22 | 18s ± 5 | 46% |
| abdominal pos. | 0:03:43 | 4 | 0 | 22s ± 7 | 1% |
| upright | 2:28:47 | 9 | 1 | 12s ± 1 | 2% |
| all | 8:00:10 | 380 | 47 | 17s ± 6 | 100% | sum of all position changes = 23
mobility index (position change/hour) = 3 b)

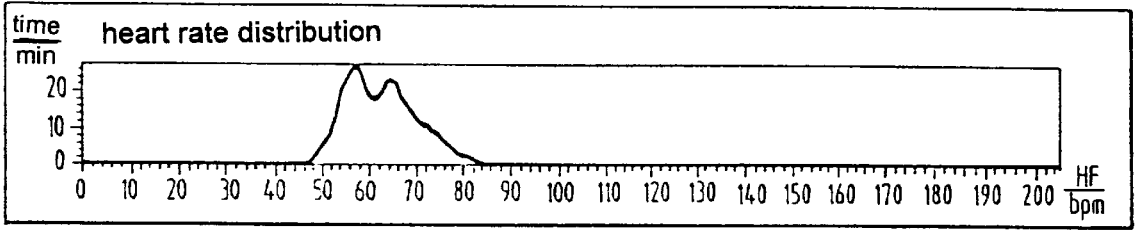

heart rate distribution c)

| E. snoring, heart rate |||| 
|---|---|---|---|
| snoring | evaluation period absolute | relative | heart rate |
| without snoring | 0:06:26 | 1% | 66 bpm ± 2 |
| with snoring | 0:11:31 | 2% | 66 bpm ± 3 |
| with loud snoring | 7:42:13 | 96% | 63 bpm ± 8 |
| sum | 8:00:10 | 100% | 63 bpm ± 8 |
| average heart rate increase with snoring /without snoring: 96.1% ||||

Fig. 6
| MAP Medizintechnik für Arzt u. Patient | POLY-MESAM S/W: V 1.1, H/W: PolyMesam |
| patient: | birthday: | PID: |
| recording: | data file: | doctor: |
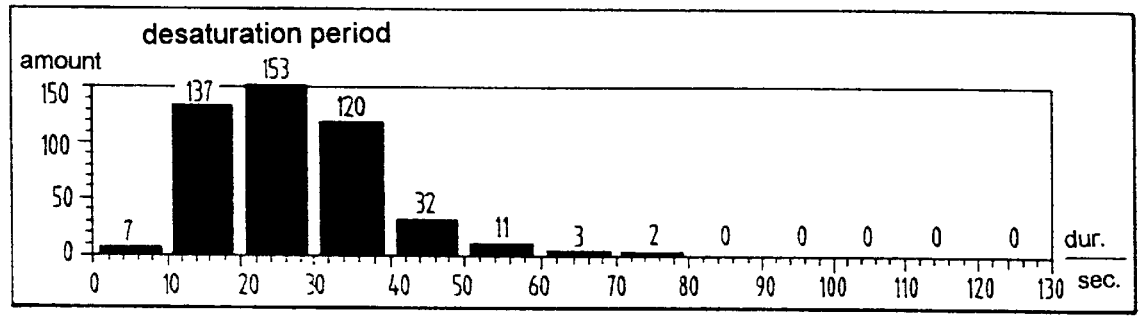
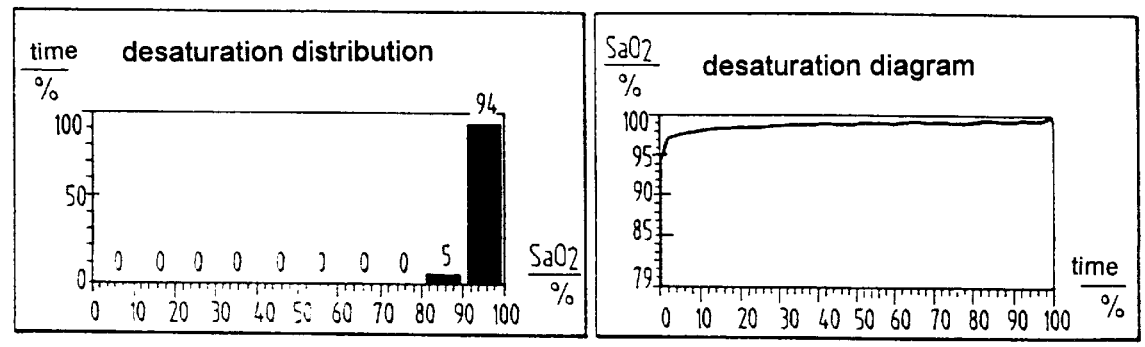

METHOD AND DEVICE FOR QUANTITATIVE ANALYSIS OF SLEEP DISTURBANCES

FIELD OF THE INVENTION

The invention relates to an apparatus and a method for the quantitative analysis of sleep disturbances or disorders, in particular for the stationary and ambulant detection, recording and analysis of sleep-related respiratory disturbances, cardiac rhythm disturbances, myoclonia, variations in blood pressure, depth of sleep parameters, movement parameters and disturbance or disorder parameters.

BACKGROUND OF THE INVENTION

Due to the increasing number of people suffering from sleep disorders and the related overburdening of sleep laboratories dealing with these disorders, the examination and measurement of disturbances by means of mobile apparatuses has been shifted from the stationary sector to the ambulant sector. The patients are told how to deal with the sensors connected with these apparatuses and, after the measuring time, return the mobile recording apparatus to the doctor attending them; the doctor then analyzes the recorded measuring signals to subsequently make a diagnosis. This ambulant method is very inexpensive due to the high time requirements related with a measurement and, furthermore, the results are not influenced by performing the measurements in a surrounding which is strange for the patient.

Such a mobile recorder is described in EP-A-0 356 603. This recorder allows the recording of measuring signals by means of eight channels, their storage and subsequent analysis in a computer. In this connection, it is possible to program the recorder in different ways in order to reduce the number of measured data by a preselection and to limit the data to desired measuring data depending on the clinical picture or the purpose of the diagnosis. By this different programming, the measurement can be adapted to different frame conditions.

The measurement of different parameters for the detection of sleep disturbances is discussed in DE-A-41 38 702. The apparatus disclosed therein comprises sensors for detecting the heart potential, the respiratory and snoring sounds, the degree of oxygen saturation of the blood and the patient's body position. An analysis of the measured results allows the diagnosis of apnea. However, this analyzing apparatus is limited to only one application purpose, namely the detection of sleep disturbances (apnea) and, with the mentioned sensors, comprises analyzing instruments designed for this very purpose only. In particular, although sleep-related respiratory disturbances can be detected, the "side effects" related therewith, such as cardiac rhythm disturbances, cannot be detected.

With respect to the prior art, reference is also made to DE 92 04 190 U1, DE 32 48 222 A1, DE 39 21 784 A1, U.S. Pat. No. 3,734,086, DE 92 00 249 U1 and Kurz, Roland: "Medizinische Meßtechnik und Biosignalverarbeitung in der kardiologischen Diagnostik" [Medical Measuring Technique and Biosignal Processing in Cardiological Diagnostics], M.-G.-Schmitz-Verlag Gießen 1984, pages 122–129, ISBN 3-922 272-23-1.

BRIEF SUMMARY OF THE INVENTION

It is the object of the invention to provide an apparatus and a method for the quantitative analysis of sleep disturbances by means of which disturbances occurring during sleep can most exactly and completely be detected, so that in addition to the analysis of these disturbances also disturbances of other body functions resulting therefrom can be detected. In particular, the apparatus and method is meant for detecting sleep disturbances based on cardiac rhythm disturbances (so-called "apnea-associated cardiac rhythm disturbances"). These objects are achieved with the features of the claims.

In achieving these objects, the invention is based on the following basic idea.

For a quick and exact analysis of sleep disturbances and disturbances related therewith, it is very important which body signals are recorded and how many parameters are necessary for indicating the cause of the disturbances by a correlation or comparison of these signals. For this reason, in the present invention it is possible to measure the heart potential, the oxygen saturation of the blood, the body position, movements of the body, respiratory sounds, the positive pressure respiration, the respiratory flow, the respiratory activity and other electro-physiological measuring values by means of different sensors and to thus provide comprehensive data material for the analysis. The measured signals are supplied by the sensors to a mobile recorder, intermediately stored therein and, after the measuring cycle, read out and processed by a computer, e.g. a personal computer. For this, the recorder comprises a storage card as an external storage. This storage card is used for storing the signals and is, moreover, programmed for the subsequent application prior to the measurement. In this way, a purposeful selection of specific sensors is possible by selecting a respective program. This division into two hardware components allows any stationary or mobile use of the apparatus. For the analysis of the measured data, these data may on the one hand be directly displayed on the monitor of the PC in an unamended form, wherein of course desired time domains may be selected, and, on the other hand, these data are, however, also used as a basis for an evaluation by means of which further parameters may be detected. For example, the heart potential signal is supplied to a heart rate analyzer which thus determines the changes in the heart rate directly or by means of a correlation with other measured values or histograms. Moreover, the measured values are edited by means of suitable computational operations so that they can, e.g., be displayed in the form of tables or histograms. In particular, the oxygen saturation of the blood, the patient's position changes, snoring activities and respiratory disturbances can in this way be displayed clearly and expressively.

In therapy control, the positive respiration pressure of the positive pressure respirators is also registered. By a correlation or comparison of these data, e.g. sleep disturbances, respiratory disturbances, cardiac rhythm disturbances can be detected. In particular, it is advantageous that cardiac rhythm disturbances caused by sleep disturbances can be detected. This very kind of cardiac rhythm disturbances cannot be treated sufficiently by common methods such as anti-arrhythmic drugs or cardiac pace-makers. However, if a causal relation between these cardiac rhythm disturbances and the sleep disturbances can be detected, the cardiac rhythm disturbances can causally be eliminated by treating the sleep disturbances.

In order to increase the efficiency of the analysis, disturbance signals of the environment and a decrease in the distribution voltage are taken into account for the evaluation. Monitoring the distribution voltage prevents a data loss since in case of a voltage drop the data detected up to that time are stored and can be used for the evaluation. The disturbance signals inputted via the sensor cables are filtered in different frequency ranges and can then be compared with the useful signals in order to thus locate those signal parts in the useful signals which were caused by the disturbance fields. Thus, these disturbance parts do not have to be taken into consideration during the analysis.

Moreover, alarm generators are provided which alarm when a predetermined threshold value of the oxygen saturation of the blood or the heart rate is reached and thus allow the use of the apparatus also for high-risk patients.

The recorder is advantageously provided with a real-time clock so that, on the one hand, a real-time display of the signals and, on the other hand, the use during a very special time period is possible. For this, the recorder is changed into a "sleep" mode and the measurements do not start before a desired time. This has particular advantages when the recorder is preset in an institute and then sent to the patient.

As a special embodiment, the present invention also allows the recordation of EEG signals and blood pressure values of other mobile apparatuses. Thus, by the EEG signal also the depth of sleep can be detected.

A further advantage of the apparatus according to the invention can be seen in that by a comparison of the heart potential signal and the signal of the measurement of the oxygen saturation of the blood, the pulse rate or its change can be detected. Since it correlates with the variations in the blood pressure, an additional blood pressure measurement is no longer necessary for detecting these variations.

The apparatus according to the invention now allows a method for the quantitative analysis of sleep disturbances in which a programmed recorder records and stores signals recorded by measuring sensors. These data are subsequently (in the case of a mobile use) or simultaneously (stationary) transferred to a computer and processed therein. The measured and processed data are then displayed graphically.

BRIEF DESCRIPTION OF THE DRAWINGS

In the following, the invention is explained in more detail in connection with the drawings in which FIGS. 1a) and b) show graphical illustrations of a selection of the detected values as a function of time in two different time intervals, FIGS. 2 to 6 show illustrations of a selection of analysis results in the form of tables (FIGS. 2b, 3b, 3d, 4a, 4c) and diagrams (FIGS. 3a, 3c, 4b, 5, 6) with patient data (FIG. 2a)

DETAILED DESCRIPTION OF THE INVENTION

Figure 7:
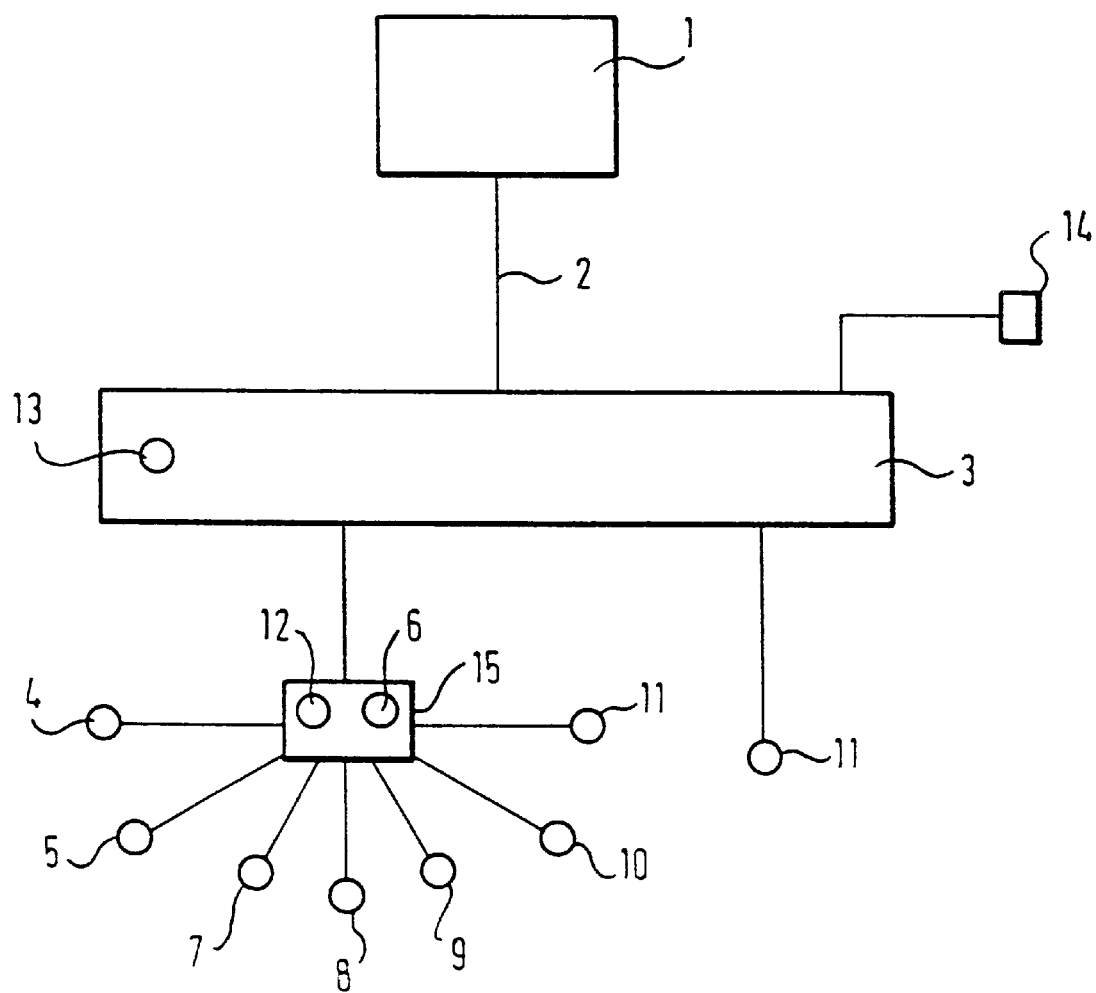
FIG. 7 shows a schematic illustration of the apparatus according to the invention.

In the following, the sensors used and the measuring signals provided by them are first explained in more detail. A schematical illustration of the apparatus according to the present invention can be taken from FIG. 7.

The patient's respiratory sounds and snoring sounds are recorded by an electret microphone 4 which must be positioned at the larynx. The frequency range of this microphone is between 50 and 1500 Hz. The analog signal curve provided by this microphone is rectified and filtered, then the enveloping curve is scanned and digitized by a frequency which can be preselected via a configuration menu. The respiratory flow (flow in FIG. 1) is simultaneously taken from the nose and mouth by means of a thermistor 5 or a thermoelement. For this, a sum signal is formed which, on the one hand, allows the determination of the respiratory frequency and, on the other hand, the detection of the respiratory amplitude. Thus, together with the sensors for thorax and abdomen, which will be described in the following, occurring apnei can be differentiated well. The thoracic respiratory movement is recorded by a piezoceramic sensor 6 contained in a distribution box 15 in which various measuring cables meet. The distribution box contains pre-amplifiers for the measuring sensors. For the abdominal respiratory movement a piezoceramic sensor 7 is used, too. For registering the movements of the extremities, at least one actography sensor 8 is provided. This sensor can, e.g., be positioned on the arm or leg and, if a second sensor is used which is connected to the first sensor via a Y-separating-filter, the movements of both the arms and/or legs can be detected simultaneously. By means of these actography sensors, periodic movements of the extremities can be detected, which can be allocated as compared to heart rate variations. Electrocardiography (ECG) is used for measuring the heart potential. For this, the three electrodes 9 are positioned on the standardized locations on the body. The analog heart potential is digitized and stored as an ECG signal. At the same time, the analog ECG signal is supplied to a peak value detector to allow the determination and storage of the heart rate based on the time intervals between the R-peaks. The oxygen saturation of the blood is measured by a pulse oximeter 10, the sensor of which is positioned on the patient's finger. Moreover, like in a nasal hyperbaric oxygen therapy, during the measuring period the positive pressure respiration can be detected directly on the mask by means of a pressure sensor 11. Together with a pre-amplifier electronic circuitry and a separate power supply, the pressure sensor is incorporated into a separate housing. The measuring range lies between −10 mbar and 30 mbar. Finally, the body position can be detected by a position sensor 12 consisting of, e.g., four mercury switches. This position sensor stably shows 5 positions: right, left, supine position, abdominal position, upright. This position sensor, too, can be integrated in the distribution box. The position sensor allows the determination of the actual time of the sleep position and the times of uneasy sleep; thus, different apnea phases can be detected depending on the body position, and also artifacts can be allocated well. A special advantage can be seen in that both the position sensor and the piezo sensor for the thoracic respiratory movement are integrated in the distribution box; thus, the number of measuring points on the patient's body is reduced.

The following is a short description of a measuring process.

Prior to the actual ambulant or stationary operation, the apparatus is programmed for the respective application via a flow chart on the storage card provided in the recorder 3. During the recording, all physiological signals are stored on this storage card. The recorder is programmed by reading-in a flow chart for an internal microprocessor from the storage card, which takes place immediately after inserting the storage card. The recorder has a real-time clock and can be programmed to start on a predetermined time point or date. After programming, the recorder changes into a power-saving "sleep mode" and is waked by the real-time clock at the programmed starting time and date and switched off again at a stopping time. Depending on the medical questions and the configuration necessary therefor (channel number, scanning rates, starting time, stopping time, patient data, etc.), the flow charts are written on the storage card by a computer 1. Depending on the use of the storage cards (PCMCIA-ATA-standard), storage capacities between 1.8 Mbytes and 170 Mbytes can be used. Thus, the different storage capacities of the storage cards allow a configuration of the physiological signals with different scanning rates and with different recording times via the flow charts. After reading-in in the computer, the physiological data stored on the storage card are stored without any falsification as rough data and can at any time be newly analyzed and displayed. In the stationary real-time operation, the recorder is directly connected with the computer via a serial interface 2 which is used for the data transfer to the PC during recording.

In order to reduce the possibility of a faulty diagnosis caused by malfunction or a patient's inappropriate use in the ambulant operation, the doctor can afterwards control the correct course of the recording. For this, e.g., the supply voltage is recorded, wherein the recording is stopped when the supply voltage falls below a predetermined value. The data recorded up to that time, however, can all be evaluated.

After the application, the functionality of the recorder and the sensors is controlled by the real-time display on the computer. If no computer is available, application control takes place by means of LED-lamps provided on the front surface of the recorder. After reading-in the flow chart, a test mode lasting five minutes is started, in which the LED-lamps light upon application of a respectively allocated sensor. This test program can be re-started when a marker key 13 is pressed. The marker key is provided for enabling the patient to mark specific events, such as e.g. waking up in the night.

Figure 1:
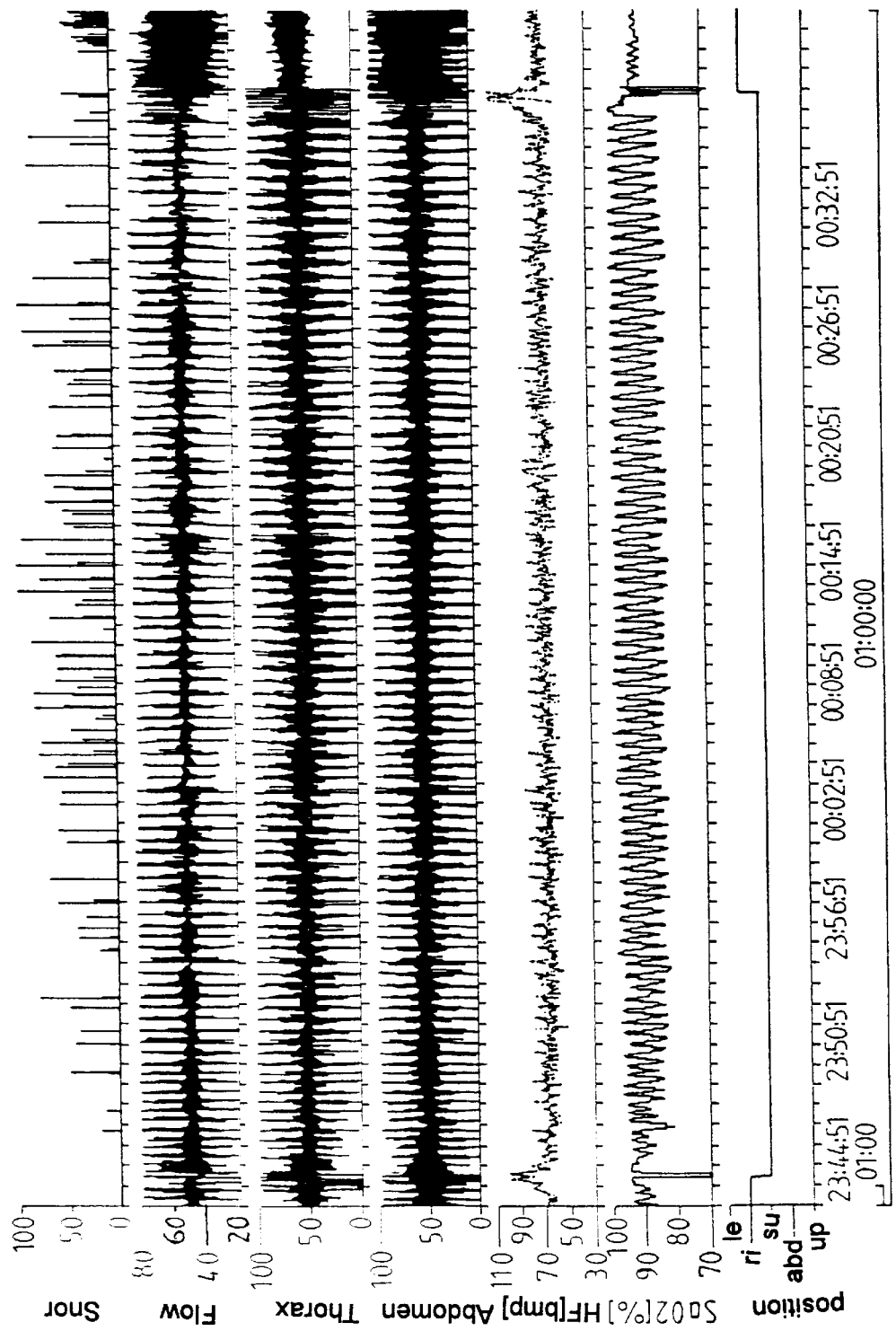
Figure 5:
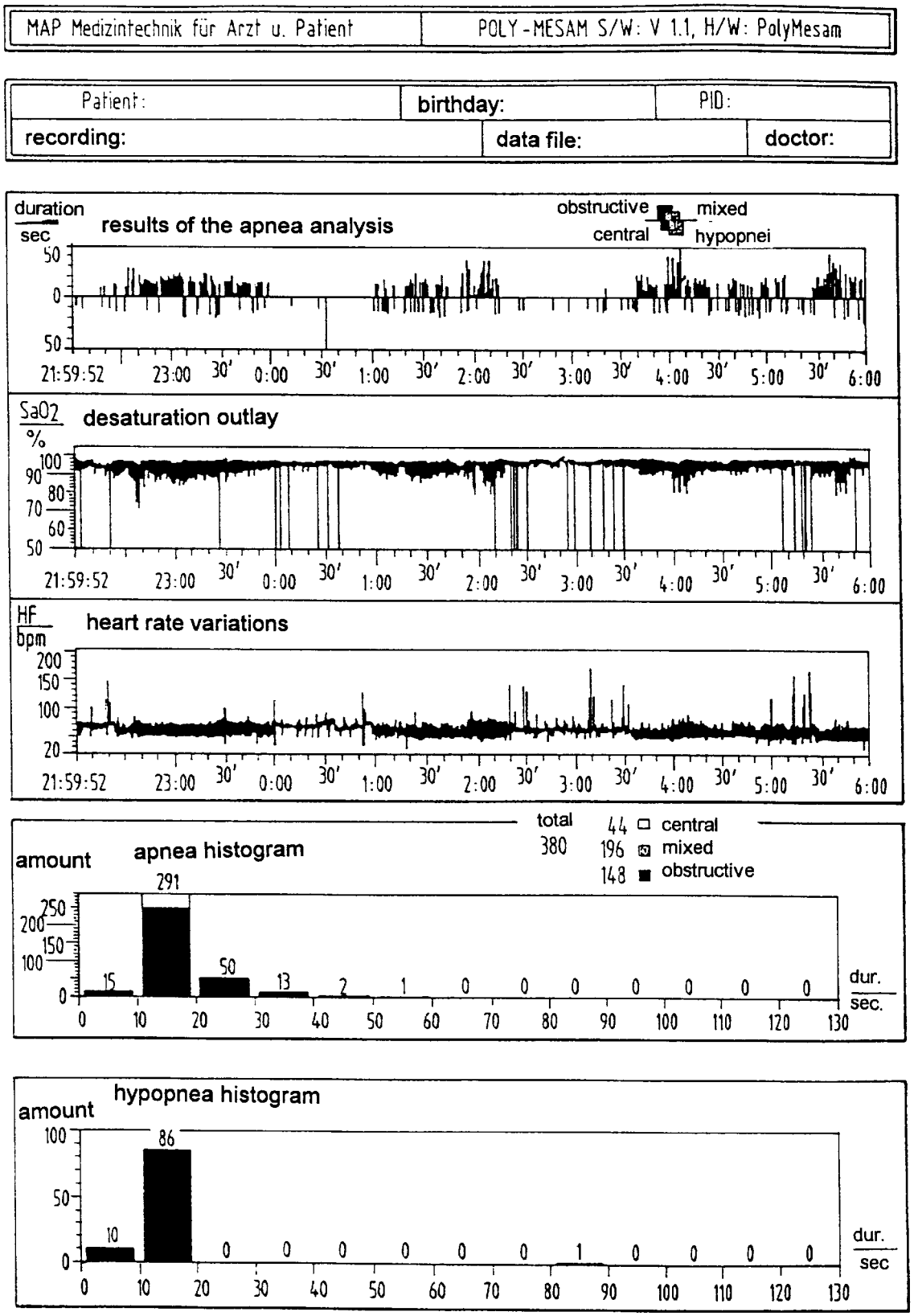

FIGS. 2 to 6 exemplarily show the evaluation of a measuring cycle, wherein the data are illustrated in different ways. Signals, which are expressive already in the rough version, are illustrated for a desired time period as a function of time. The data of the measurement of the oxygen content of the blood, the position sensors, the electret microphone and the piezoelectric sensors for detecting the respiratory activity are evaluated in accordance with statistical methods and illustrated in the form of tables and histograms. The heart rate distribution (FIG. 4) is also illustrated as a graph. Moreover, as shown in FIG. 1, a mere time dependency of the data can be illustrated. In particular, the temporal courses of the measured signals can be illustrated in any desired combination, and a combined display of respiratory and cardiological parameters allows an allocation of specific cardiac rhythm disturbances to the occurring sleep disturbances. These cardiac rhythm disturbances are best observed in the temporal illustration of the heart rate and qualitatively and quantitatively detected during evaluation. The heart rate variations are detected automatically, and a heart rate index is calculated therefrom. To distinguish cyclical heart rate variations induced by sleep apnea from those variations induced by myoclonus, the heart rate signal is compared with the signal of the actography sensor. The respiratory events, i.e. the sleep-related respiratory disturbances, are also quantitatively analyzed during evaluation and described by different indices calculated therefrom. These are also illustrated in the form of a table, as evident from the bottom of FIG. 2. By the application of special evaluation algorithms which will be described later, the present invention allows a differentiation between hypopnea and obstructive, central or mixed apnea. Moreover, in the automatic analysis of apnea and hypopnea, the recorded pressure variations in the nasal hyperbaric oxygen therapy are used instead of the respiratory flow signal, thus permitting an exact therapy control.

By means of the comprehensive data material made available for the doctor by the present invention, the doctor is in a position to make an exact diagnosis with respect to sleep disturbances, respiratory disturbances and cardiac rhythm disturbances. The attended patient can thus be treated purposefully.

As an example, the following correlations, which can be performed automatically within the scope of the invention, are possible:

1. A correlation between snoring sounds and oxygen reduction indicates an obstructive apnea.
2. A correlation between rhythmic leg movements (PLMs, myoklonus) and heart rate, without snoring and without oxygen desaturations, indicates an influence of leg movements on the cardiovascular system with arousal effect.
3. An arrhythmia without a correlation to another signal indicates an absolute arrhythmia.
4. An arrhythmia synchronous to the respiratory signals indicates sinus arrhythmia and apnea-associated arrhythmia.
5. A compensatory arrhythmia without correlation to other signals indicates ventricular extrasystoles.
6. A regular oxygen desaturation with synchronous interruption of flow, as well as movements of the thorax and abdomen indicate a central apnea.
7. Long-lasting oxygen desaturations with a possibly unspecified reduction of the respiratory parameters and a possibly slow change of the heart rate indicate an obstructive lung decease.
8. A strong apnea with strong synchronous oxygen desaturations and slight but synchronous heart rate variations indicates an autonomic neuropathy (e.g. in the case of an advanced diabetes).
9. A decreasing heart rate after the change from the upright into the horizontal position indicates falling asleep. In case of a simultaneous apnea or PLM, the time point at which the patient falls asleep can be detected with only a slight error tolerance.
10. Irregular changes occurring approximately each one and a half hours simultaneously in all signals and lasting for approximately 20 to 40 minutes, indicate REM sleep (dream sleep).
11. Regular snoring without oxygen desaturation but with cyclical heart rate increases indicates an UARS (Upper Airways Resistance Syndrome).
12. The difference between the absolute values of thoracic and abdominal movements is detected as the obstruction rate and illustrated in a diagram (e.g. in an additional channel).

In the following, the evaluation algorithms referring to the heart rate analysis, the algorithms for the detection of apnea and hypopnea and the algorithm for the detection of oxygen desaturations are discussed.

The physiological data are, on the one hand, evaluated visually by means of the rough data and, on the other hand, by means of the automatic evaluation programs on the computer.

The automatic heart rate analysis

Algorithm for the detection of heart rate variations (apnea-associated sinus arrhythmia)

In this case, the R peak distance, the so-called tachogram, is used.

The algorithm works off the table with the heart rate values as follows. The respective heart rate is indicated by $h_i$, $\Delta h_i$ indicates the differences from $h_i$.

Algorithm for the detection of heart rate increases
n=maximum duration for the increase
for i=1, ..., n
$\Delta h_i = h_i - h_{i-1}$ Taking up $\Delta h_i$ into the integration buffer. The integration buffer is an n-dimensional vector, which is initialized with zeros.

$$\text{intergration buffer} = \begin{bmatrix} \Delta h_1 \\ \vdots \\ \Delta h_i \\ 0 \\ \vdots \\ 0 \end{bmatrix}$$

Calculating the sum by means of the individual vector elements $$\text{Integral} = \sum_{k=0}^{n} \Delta h_k$$

Case distinction
  Integral<0:
    The heart rate curve has descended. The integration buffer is initialized with zeros.
    Integration buffer [i]=0; i=1, ..., n
  0<integral<threshold:
    The heart rate curve has ascended, but not enough.
  Integral>threshold:
    The heart rate curve has ascended by at least the threshold value. The first citerion for an event is fulfilled.
Search for the maximum
From the starting point of the ascent, the maximum is searched for. This is achieved by comparing the heart rate values.
for n=1, ..., end of table
  read-in value>present maximum:
    value>maximum
    new value is read in
  read-in value<present maximum:
    =value maximum=≦discontinuation threshold:
      The heart rate curve has descended again, but not so much that the ascent could be regarded as finished. The search for the maximum is continued.
    =value maximum=>discontinuation threshold:
      The heart rate curve has descended again, namely by at least the value of the discontinuation threshold. Thus, the maximum has been detected. Starting out from the detected maximum, the starting point and the finishing point of the heart rate variation are now searched for.
Search for the starting point of the ascent
Going backwards in time and starting out from the detected maximum, the starting point of the ascent, the 1st minimum, is now searched for. The search takes place analogously to the search for the maximum. The table values are gone through backwards until the end of the preceding ascent is reached, at the most, however, up to the "finishing point of the search interval for the first minimum", a value which can be preselected by the user.
for last minimum, ..., maximum:
  read-in value<present 1st minimum:
    value=1st minimum
    new value is read in
  read-in value>present 1st maximum:
    =value—1st minimum=≦discontinuation threshold:
      The heart rate curve has ascended again, but not so much that the starting point of the ascent could be regarded as having been reached. The search for the starting point is continued.
    =value—1st minimum=>discontinuation threshold:
      The heart-rate curve has ascended again, namely by at least the value of the discontinuation threshold. Thus, the starting point of the ascent has been detected. Now, the finishing point of the ascent is determined in the next step.
Search for the finishing point of the heart rate increase
Going forward in time and starting out from the detected maximum, the finishing point of the ascent, the 2nd minimum, is now searched for. The search takes place analogously to the search for the 1st minimum. The table values are gone through forward until a minimum is detected, at the most, however, up to the "finishing point of the search interval for the second minimum", a value which can be preselected by the user.
for i=1, ..., n:
  read-in value<present 2nd minimum:
    value=2nd minimum
    new value is read in
  read-in value>present 2nd minimum:
    =value—2nd minimum=≦discontinuation threshold:
      The heart rate curve has ascended again, but not so much that the finishing point of the ascend could be regarded as having been reached. The search for the finishing point is continued.
    =value—2nd minimum=>discontinuation threshold:
      The heart rate curve has descended again, namely by at least the value of the discontinuation threshold. Thus, the 2nd minimum has been detected.

Figure 8:
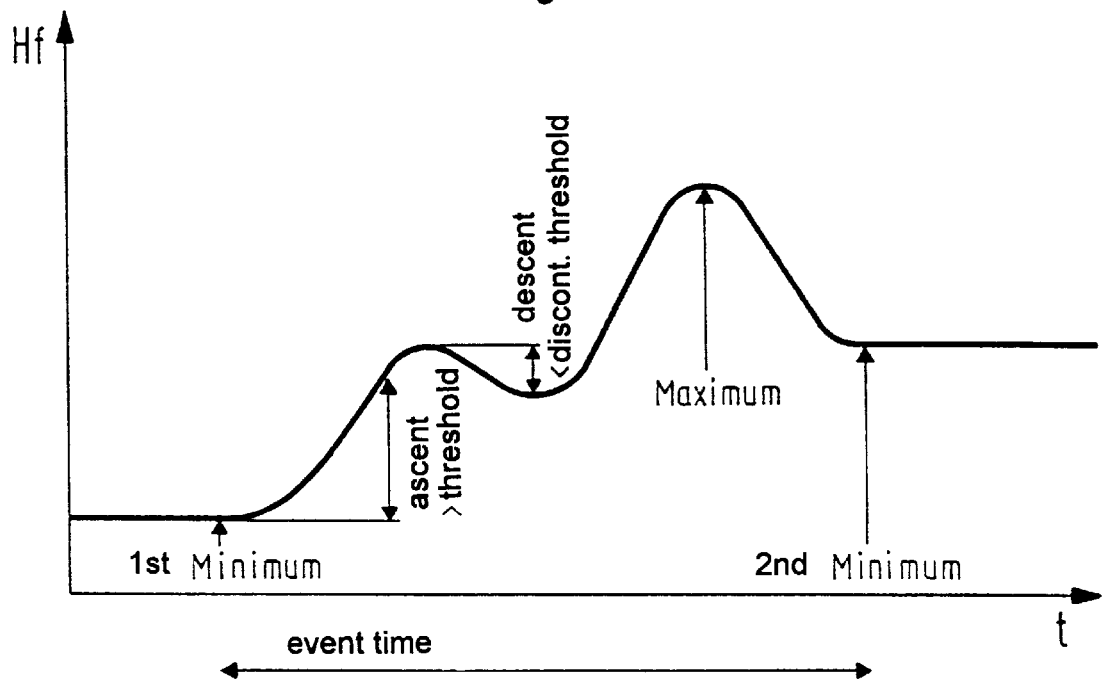
FIG. 8 shows the evaluation of a first heart rate signal.

Analogously to the $SaO_2$ analysis, also in this case the individual parameters play an important role. Since the heart rate signal is much more complex than the $SaO_2$ signal, specific phenomena occur more intensely. FIG. 8 exemplarily illustrates the heart rate analysis.

The analysis parameters of the heart rate analysis
In this case, too, the individual preselectable parameters are once again explained in detail.
Minimum heart rate increase $\epsilon[1, 30]$
This value determines how much the heart rate curve has to ascend in order to start the search for the maximum. In the algorithm, this value is the integration threshold.
Maximum time interval for the Hf increase $\epsilon[1, 250]$
This value limits the time period in which the descent of the Hf curve has to take place. In the algorithm, it determines the dimension of the integration buffer.
Discontinuation threshold for min-max-search $\epsilon[1, 10]$
The discontinuation threshold is the discontinuation criterion for a minimum or maximum search when the Hf curve is changed for this amount.
Minimum and maximum event time $\epsilon[1, 250]$
In the long run, these two parameters are decisive for whether or not a detected heart rate increase is taken up in the event list as an event. In order to be taken up as an event, the following must apply for the duration of the increase:

min. event time $<(t_{2nd}$ min$=t_{1st}$ min)$<$max. event time

Search interval for the maximum $\epsilon[1, 30]$

It limits the search environment for the search for the maximum thereby starting out from a present and thus temporary maximum.

Search interval for the first minimum $\epsilon[1, 30]$

This search interval limits the search environment for the search for the starting point of the heart rate increase. This interval is a second discontinuation criterion in addition to the discontinuation threshold. It prevents the algorithm from running to death when the heart rate meets a plateau (FIG. 8).

Search interval for the second minimum $\epsilon[1, 30]$

Figure 9:
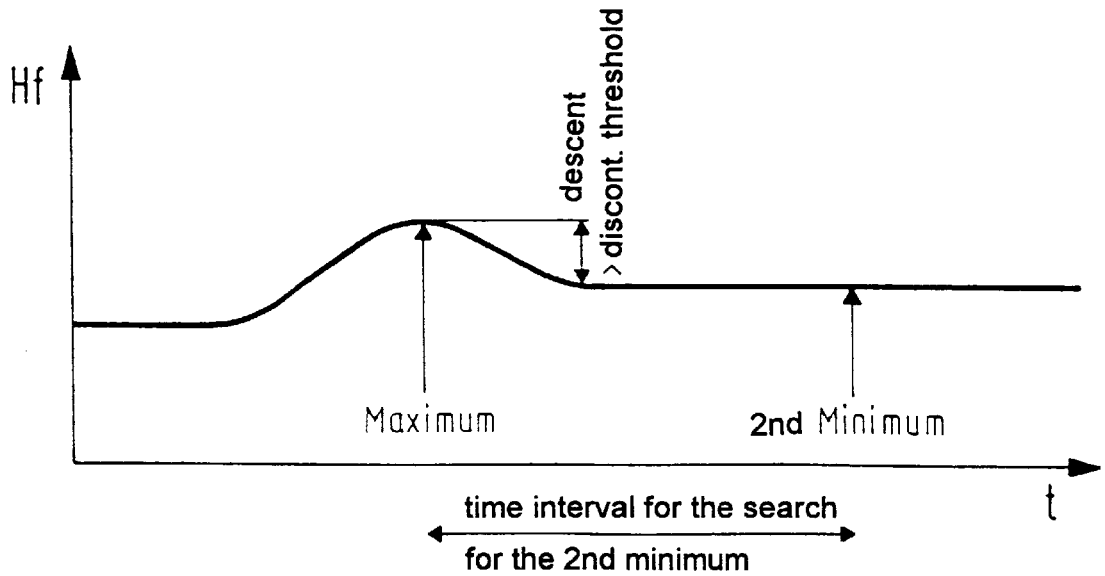
FIG. 9 shows the evaluation of a second heart rate signal, FIG. 10 the evaluation of a respiratory signal, FIG. 11 the evaluation of a first signal of the oxygen saturation of the blood from the pulse oximeter, and FIG. 12 the evaluation of a second signal of the oxygen saturation of the blood from the pulse oximeter.

This search interval limits the search environment for the search for the finishing point of the increase. This interval is a second discontinuation criterion in addition to the discontinuation threshold. It prevents the algorithm from running to death when the heart rate curve meets a plateau (FIG. 9).

The basic parameter selection is:

| | |
|---|---|
| minimum heart rate increase: | 8 |
| discontinuation threshold for minimum-maximum-search: | 8 |
| search interval for the maximum: | 30 s |
| search interval for the 1st minimum: | 10 s |
| search interval for the 2nd minimum: | 10 s |
| minimum event time: | 5 s |
| maximum event time: | 150 s |

The respiratory channels

Algorithm for the detection of apnea and hypopnea

The algorithm takes place in three steps:

filtering the present dates calculating the limiting values performing the analysis on the basis of the edited data It is necessary to filter the data since the signal of the respiratory channels is complicated and susceptible to disturbances. Filtering takes place floatingly or smoothly, for one second each; this corresponds to 250 sampling values.

Filtering the data:

The sampled values of the respective respiratory channel are represented by $f_i$.

$$\frac{\text{for } i = 1, \ldots, 250}{\Delta f_i = f_i - f_{i-1}}$$

Taking up $\Delta f_i$ into the difference buffer. The difference buffer is an 250-dimensional vector which is initialized with zeros.

$$\text{difference buffer} = \begin{bmatrix} \Delta f_1 \\ \vdots \\ \Delta f_i \\ 0 \\ \vdots \\ 0 \end{bmatrix}$$

Calculating the sums for the integral buffer $$sum_k = \sum_{k=1}^{i} \Delta f_i$$

$$\text{integral buffer} = \begin{bmatrix} sum_1 \\ \vdots \\ sum_k \\ 0 \\ \vdots \\ 0 \end{bmatrix}$$

These values are used for the following calculations.

An apnea or hypopnea is characterized in that the respiratory curve descends by a certain percentage as compared to the previous respiration. Since respiration is always a sinusoidal curve whose amplitude varies even in the case of healthy persons, the average value has to be calculated by means of the previous breaths in order to detect a breath decrease. This is done by means of the following algorithm:

Algorithm for the detection of apnea/hypopnea limits

The average value is calculated by means of the minima and maxima of the last 10 breaths.

Detection of the maximum:

$sum_i > 0$:

if $sum_{i+1} >$ max$>0$, i.e. the respiratory curve is still ascending, max$=sum_{i+1}$ if $sum_{i+1} < 0$, i.e. the curve has already exceeded the maximum, the last calculated maximum is valid.

Detection of the minimum:

$sum_i < 0$:

if $sum_{i+1} <$ min$<0$, i.e. the respiratory curve is still descending, min$=sum_{i+1}$ if $sum_{i+1} > 0$, i.e. the curve has already exceeded the minimum, the last calculated minimum is valid.

By means of the amounts of the calculated minima and maxima, the average value is calculated:

$$\text{average} = \frac{\sum_{i=1}^{5} |\min_i| + \max_i}{10}$$

The apnea/hypopnea limits are then calculated from $$\text{limit} = \frac{\text{event threshold} * \text{average}}{100}$$

wherein the event threshold can be selected in percentages.

All auxiliaries necessary for the analysis are now ready.

Algorithm for the detection of apnea and hypopnea for i=1, . . . , 250

If $==sum_i =<$limit set counter=0 and start to count.

If $==sum_i ==>$limit check how far the counter has run. If minimum event time$<$counter$<$maximum event time an apnea or hypopnea has been detected.

Figure 10:
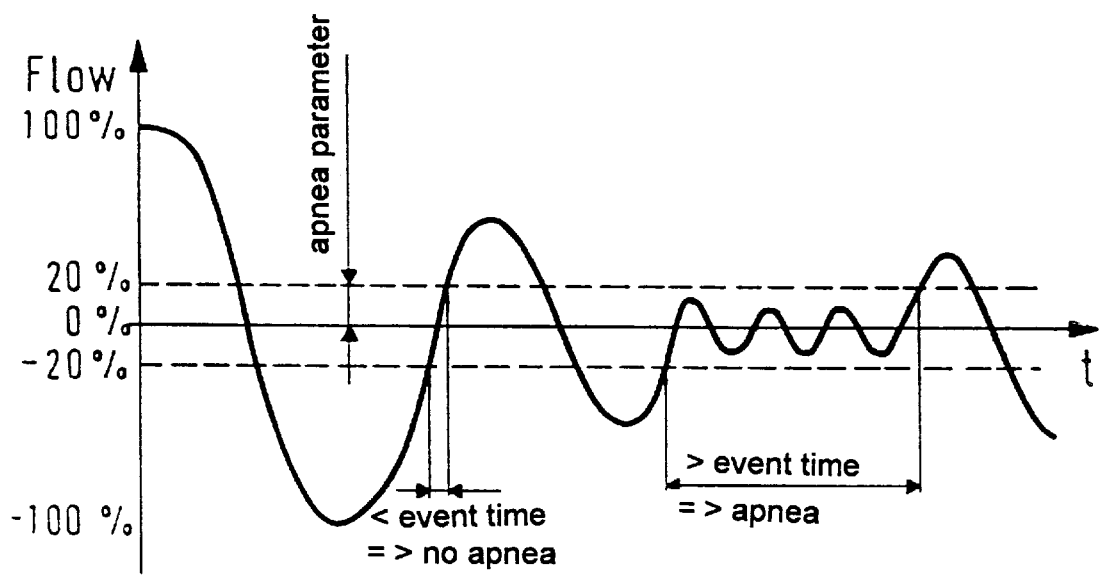

This analysis is performed on all respiratory channels. Obstructive and central apnea are differentiated on the basis of the thoracic and abdominal activity. If the respiratory activity decreases on the mouth and nose, the program checks whether, in correlation thereto, the thoracic and abdominal activity decreases as well. If this is the case, a central apnea is concerned. FIG. 10 illustrates the analysis for the detection of apnea.

The analysis parameter of the apnea analysis

The parameters in the apnea analysis are determined by the medical diagnosis. The following parameters can be selected:

Apnea threshold
In order to diagnose an apnea, the respiratory curve must descend by at least 80% with respect to the average value of the last ten breaths. In the algorithm, this value corresponds to the event threshold.

Minimum apnea time
This value limits the time interval in which the respiratory curve must lie below the apnea threshold. The minimum apnea time must last at least 10 seconds.

Hypopnea threshold
In order to diagnose a hypopnea, the respiratory curve must descend by at least 50% with respect to the average value of the last 10 breaths. In the algorithm, this value corresponds to the event threshold.

Minimum hypopnea time
This value limits the time interval in which the respiratory curve must lie below the hypopnea threshold.
The minimum hypopnea time must last at least 10 seconds.

Central apnea threshold
In the case of a central apnea, the amplitude of the thoracic and abdominal signals must descend by at least 80% with respect to the average value of the last 10 breaths.

Minimum central time
This value limits the time interval in which the thoracic and abdominal curves must lie below the central apnea threshold. The minimum central apnea time must last at least 5 seconds.

Maximum duration
This value limits the maximum duration of a significant amplitude reduction for an event.
Oxygen saturation channel
Algorithm for the detection of desaturations The aim of the algorithm is the detection of oxygen desaturations. Since the oxygen saturation is sampled very high, a data reduction is necessary for a quick analysis. For this data reduction a table is made which contains the average value for a second. This does not mean a great information loss since during a second the oxygen saturation of the blood changes little as compared to the heart rate. The algorithm then searches this table for significant events.

In this case, $S_i$ means the respective $SaO_2$ value from the table, and $\Delta S_i$ means the difference from $S_i$.
Algorithm for the detection of oxygen desaturations
n=maximum duration for the descent
for i=1, ..., n
$\Delta S_i = S_i - S_{i-1}$
Taking up the $\Delta S_i$ into the integration buffer. The integration buffer is an n-dimensional vector which is initialized with zeros.

$$\text{integration buffer} = \begin{bmatrix} \Delta S_1 \\ \vdots \\ \Delta S_i \\ 0 \\ \vdots \\ 0 \end{bmatrix}$$

Calculating the sum by means of the individual vector elements $$\text{integral} = \sum_{k=0}^{n} \Delta S_k$$

Case distinction
Integral>0:
The $SaO_2$ curve has ascended, i.e. no desaturation is indicated. The integration buffer is initialized with zeros.
Integration buffer [i]=0; i=1, ..., n
Threshold>integral>0:
The $SaO_2$ curve has descended but not so much that a desaturation could be concerned.
Integral<threshold:
The $SaO_2$ curve has descended by at least the threshold value. The first criterion for a desaturation is fulfilled.
Search for the minimum
Starting out from the descent, it is now searched for the minimum. This is achieved by comparing the $SaO_2$ values.
for n=1, ..., end of table
read-in value<present minimum:
value=minimum
new value is read in
read-in value>present minimum:
=value minimum=≤discontinuation threshold:
The $SaO_2$ curve has ascended again, but not so much that the desaturation could be regarded as finished. The search for the minimum is continued.
=value minimum=>discontinuation threshold:
The $SaO_2$ curve has ascended again, namely by at least the value of the discontinuation threshold. Thus, the minimum has been detected. Starting out from this detected minimum, the starting point and the finishing point of the desaturation are now searched for.
Search for the starting point of the desaturation Going backwards in time and starting out from the detected minimum, the starting point of the desaturation, the 1st maximum, is now searched for. The search takes place analogously to the search for the minimum. The table values are gone through backwards until the end of the preceding desaturation is reached, at the most, however, up to the "finishing point of the search interval for the first maximum", a value which can be preselected by the user.
for last maximum, ... ,minimum:
read-in value>present 1st maximum:
value=1st maximum
new value is read in
read-in value<present 1st maximum:
=value—1st maximum=<discontinuation threshold:
The $SaO_2$ curve has descended again, but not so much that the starting point of the desaturation could be regarded as having been reached. The search for the starting point is continued.

=value—1st maximum=>discontinuation threshold:
The SaO₂ curve has descended again, namely by at least the value of the discontinuation threshold. Thus, the 1st maximum has been detected since the previous desaturation has now been reached. In the next step, the finishing point of the desaturation is detected.

Search for the finishing point of the desaturation Going forward in time and starting out from the detected minimum, the finishing point of the desaturation, i.e. the 2nd maximum, is now searched for. The search takes place analogously to the search for the 1st maximum. The table values are gone through forwards until a maximum is detected, at the most, however, up to the "finishing point of the search interval for the second maximum", a value which can be preselected by the user.

for i=1, ... n:
read-in value>present 2nd maximum:
value=2nd maximum
New value is read in.
read-in value<present 2nd maximum:
=value—2nd maximum=≦discontinuation threshold:
The SaO₂ curve has descended again, but not so much that the finishing point of the desaturation could be regarded as having been reached. The search for the finishing point is continued.
=value—2nd maximum=>discontinuation threshold:
The SaO₂ curve has descended again, namely by at least the value of the discontinuation threshold. Thus, the 2nd maximum has been detected since the following desaturation has been reached.

Figure 11:
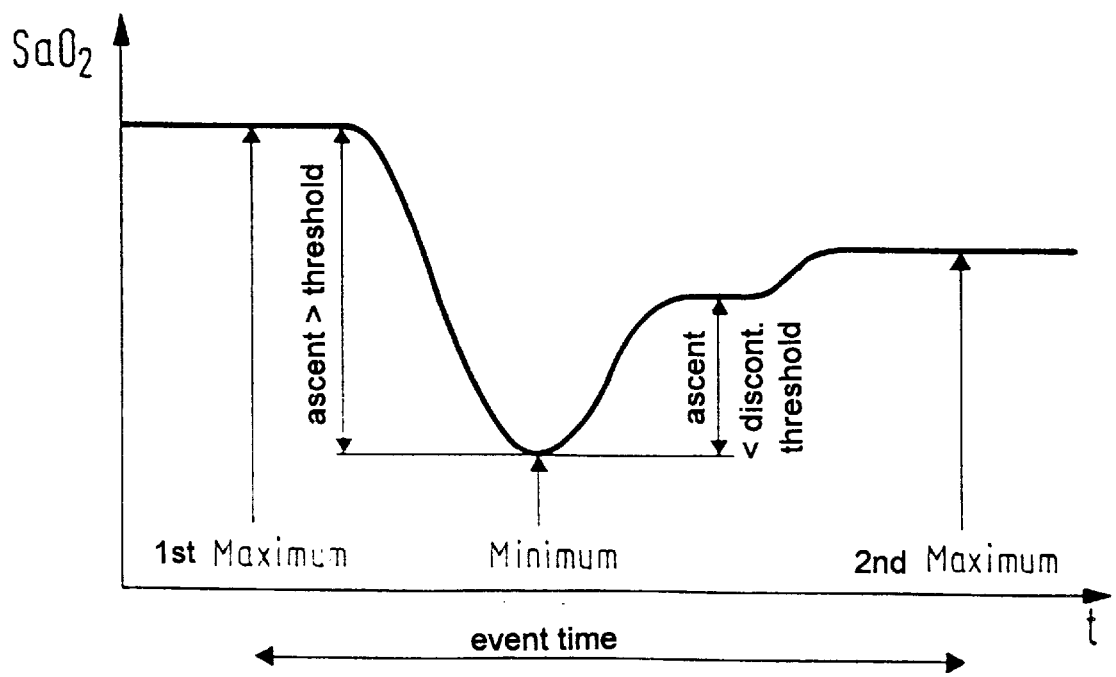

This was the description of the basic algorithm. The appropriate selection of the analysis parameters plays an important role for the effective functioning of the algorithm. The SaO₂ analysis is illustrated in FIG. 11.

The analysis parameters of the SaO₂ analysis

As already mentioned, the effectivity of the algorithm depends on the selection of the appropriate parameters. All parameters can be selected freely. In the following, they should again be explained in more detail.

Minimum SaO₂ descent $\epsilon[-10, -1]$
This value determines by how many percentage points the oxygen saturation curve must descend in order to initiate the search for the minimum. In the algorithm, this value is the integration threshold.

Minimum time interval for the SaO₂ descent $\epsilon[1, 250]$
This value limits the time period in which the descent of the SaO₂ curve must take place. In the algorithm, it indicates the dimension of the integration buffer.

Discontinuation threshold for min-max-search $\epsilon[1, 10]$
The discontinuation threshold is the discontinuation criterion for a minimum or maximum search when the SaO₂ curve is changed for this amount.

Minimum and maximum event time-periods $\epsilon[1, 250]$
In the long run, these two parameters are decisive for whether or not a detected desaturation is taken up in the event list as an event. In order to be taken up as an event, the following must apply for the time period of the increase:

min. event time$<(t_{2nd\ max} - t_{1st\ max})<$max. event time

Search interval for the minimum $\epsilon[1, 30]$
It limits the search environment for the search for the minimum thereby starting out from a present and thus temporary minimum.

Search interval for the first maximum $\epsilon[1, 30]$
This search interval limits the search environment for the search for the starting point of the oxygen desaturation. This interval is a second discontinuation criterion in addition to the discontinuation threshold.
It prevents the algorithm from running to death when the oxygen saturation meets a plateau.

Figure 12:
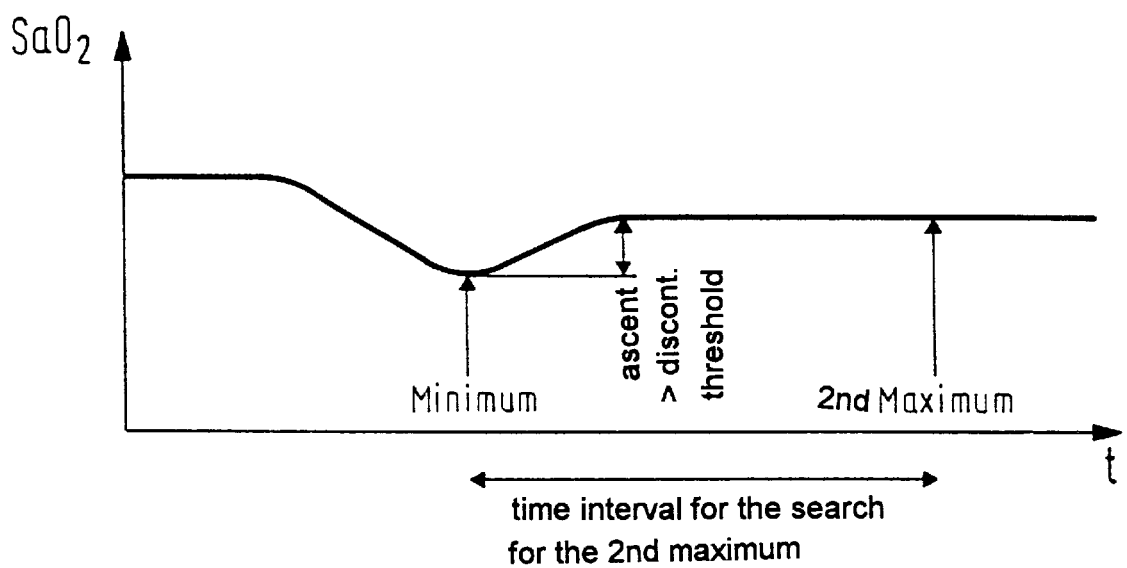

Search interval for the second maximum $\epsilon[1, 30]$
This search interval limits the search environment for the search for the finishing point of the oxygen desaturation. This interval is a second discontinuation criterion in addition to the discontinuation threshold. It prevents the algorithm from running to death when the oxygen saturation meets a plateau (FIG. 12).

The basic parameter selection is:

| | | |
|---|---|---|
| minimum SaO₂ descent: | | −4% |
| discontinuation threshold for minimum-maximum-search: | 2% | |
| search interval for the minimum: | 30 s | |
| search interval for the 1st maximum: | | 30 s |
| search interval for the 2nd maximum: | 30 s | |
| minimum event time: | | 5 s |
| maximum event time: | | 150 s |

What is claimed is:

1. Apparatus for the qualitative and/or quantitative analysis of sleep disorders, comprising a plurality of means for detecting body functions, a mobile recorder connected to the means, for recording the measured signals of the means, and a computer connected to the recorder, for storing and evaluating the measured signals, characterized by (a) means (9) for detecting the heart potential, (b) a pulse oximeter (10) for detecting the oxygen content of the blood, and (c) a means for detecting the blood pressure from the pulse wave velocity and/or the change thereof, wherein the pulse wave velocity and/or the change thereof is determined from the heart potential signal and the signal for the measurement of the oxygen of the blood.

2. The apparatus according to claim 1, wherein the means (9) for detecting the heart potential comprises three ECG electrodes.

3. The apparatus according to claim 1, wherein the pulse oximeter (10) comprises different sensors.

4. The apparatus according to claim 1, wherein at least one means from the following group is provided:

(a) means (4) for detecting respiratory sounds, (b) means (11) for detecting the positive pressure respiration, (c) means (5) for detecting the respiratory flow, (d) means (6, 7) for detecting the respiratory activity, (e) means (12) for detecting the body position, (f) means (8) for detecting the movements of the body, and (g) means for detecting electrophysiological parameters.

5. The apparatus according to claim 4, wherein the means (4) for detecting the respiratory sounds comprise an electret microphone.

6. The apparatus according to claim 1, wherein the means for detecting the body position (12) comprise four mercury switches for detecting five body positions.

7. The apparatus according to claim 1, wherein the means (8) for detecting the movements of the body comprise a piezo element.

8. The apparatus according claim 1, wherein the means (11) for detecting the pressure respiration comprise a pressure sensor.

9. The apparatus according to claim 1, wherein the means (5) for detecting the respiratory flow comprise a thermoelement.

10. The apparatus according to claim 1, wherein the means (5) for detecting the respiratory flow comprise a thermistor.

11. The apparatus according to claim 1, wherein the means (6, 7) for detecting the respiratory activity comprise a piezo element.

12. The apparatus according to claim 1, wherein the means (6) for detecting the respiratory activity are integrated in the means (12) for detecting the body position.

13. The apparatus according to claim 1, wherein also means (14) for recording external ambulant signals are provided.

14. The apparatus according to claim 1, wherein at least one alarm generator is provided.

15. The apparatus according to claim 1, wherein an alarm generator monitors the oxygen content of the blood.

16. The apparatus according to claim 1, wherein an alarm generator monitors the heart rate.

17. The apparatus according to claim 1, wherein means for taking into account noise signals are provided.

18. The apparatus according to claim 1, wherein the apparatus is programmable in accordance with a desired use.

19. The apparatus according to claim 1, wherein the apparatus is suitable for stationary or mobile operation.

20. The apparatus according to claim 1, comprising a means for correlation and/or comparison of respiratory and cardiological signals.

21. Method for the quantitative analysis of sleep disorders, characterized by the steps:

programming a recorder (3) in accordance with a desired examination, detecting the heart potential, detecting the oxygen content of the blood by means of a pulse oximeter (10), detecting the blood pressure from the pulse wave velocity and/or the change thereof, wherein the pulse wave velocity and/or the change thereof is determined from the heart potential signal and the signal for the measurement of the oxygen of the blood, recording data provided by at least one sensor, controlled by the recorder (3), supplying the data to a computer (1) for evaluation, evaluating the data by means of correlation of the signal curves and deriving further data from the recorded data, and displaying the data in the form of signal curves, tables and/or histograms.

* * * * *